United States Patent
Landis et al.

(10) Patent No.: US 9,632,032 B2
(45) Date of Patent: Apr. 25, 2017

(54) METHOD FOR MANUFACTURING A SUBSTRATE FOR SURFACE-ENHANCED RAMAN SPECTOGRAPHY

(71) Applicant: COMMISSARIAT A L'ENERGIE ATOMIQUE ET AUX ENERGIES ALTERNATIVES, Paris (FR)

(72) Inventors: Stefan Landis, Tullins (FR); Vincent Reboud, Paris (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/988,122

(22) Filed: Jan. 5, 2016

(65) Prior Publication Data
US 2016/0195475 A1 Jul. 7, 2016

(30) Foreign Application Priority Data
Jan. 5, 2015 (FR) ...................... 15 50009

(51) Int. Cl.
*G01J 3/44* (2006.01)
*G01N 21/65* (2006.01)
(Continued)

(52) U.S. Cl.
CPC ............ *G01N 21/658* (2013.01); *B82Y 15/00* (2013.01); *B82Y 20/00* (2013.01); *B82Y 30/00* (2013.01);
(Continued)

(58) Field of Classification Search
CPC .. G01N 21/65; G01N 21/01; G01N 2021/656; G01N 21/658; G01J 3/02; G01J 3/44
See application file for complete search history.

(56) References Cited

U.S. PATENT DOCUMENTS

| 2011/0140209 A1 | 6/2011 | Wang et al. |
| 2011/0305994 A1* | 12/2011 | Montelius ................ G03F 1/54 430/322 |
| 2013/0038870 A1 | 2/2013 | Lin et al. |

FOREIGN PATENT DOCUMENTS

KR  10-2011-0097354 A  8/2011

OTHER PUBLICATIONS

French Search Report as issued in French Patent Application No. 1550009, dated Nov. 26, 2015.
(Continued)

*Primary Examiner* — Abdullahi Nur
(74) *Attorney, Agent, or Firm* — Pillsbury Winthrop Shaw Pittman LLP (57) ABSTRACT

A method for manufacturing a substrate for surface-enhanced Raman spectography, includes creating a supporting structure including microstructured pattern including a top and sidewalls; depositing a multilayer on the supporting structure with the multilayer including two metal layers and an intermediate layer arranged between the two metal layers, with the intermediate layer being carried out in a material that can be selectively etched with respect to the metal layers; etching a portion of the multilayer deposited on the top of the microstructured pattern in such a way as to expose ends each layer of the multilayer; selective etching of the ends of the intermediate layers in such a way as to form cavities between the ends of two successive metal layers.

18 Claims, 11 Drawing Sheets

(51) Int. Cl.
  *B82Y 15/00*  (2011.01)
  *B82Y 20/00*  (2011.01)
  *B82Y 30/00*  (2011.01)
  *H01L 49/00*  (2006.01)
  *G01N 21/01*  (2006.01)

(52) U.S. Cl.
  CPC ............ *G01J 3/44* (2013.01); *G01N 21/01* (2013.01); *H01L 49/006* (2013.01)

(56) References Cited

OTHER PUBLICATIONS

Database WPI, Week 201172, Thomson Scientific, XP002751435, Aug. 31, 2011.
Im, H., et al., "Vertically Oriented Sub-10-nm Plasmonic Nanogap Arrays," NANO Letters, vol. 10, No. 6, Jun. 9, 2010, pp. 2231-2236.
Lin, T.-R., et al., "Coating effect on optical resonance of plasmonic nanobowtie antenna," Applied Physics Letters 97, 063106, 2010.
Ou, F.S., et al., "Hot-Spot Engineering in Polygonal Nanofinger Assemblies for Surface Enhanced Raman Spectroscopy," Nano Letters 2011, 11, pp. 2538-2542.
Choi, S., et al., "Ultradense gold nanostructures fabricated using hydrogen silsesquioxane resist and applications for surface-enhanced Raman spectroscopy," Journal of Vacuum Science & Technology B 27, pp. 2640-2643, 2009.
Zhang, Z., et al., "Manipulating Nanoscale Light Fields with the Asymmetric Bowtie Nano-Colorsorter," Nano Letters, vol. 9, No. 12, 2009, pp. 4505-4509.

\* cited by examiner

(102bis)

METHOD FOR MANUFACTURING A SUBSTRATE FOR SURFACE-ENHANCED RAMAN SPECTOGRAPHY

CROSS-REFERENCE TO RELATED APPLICATIONS

This application claims priority to French Patent Application No. 1550009, filed Jan. 5, 2015, the entire content of which is incorporated herein by reference in its entirety.

FIELD

The field of the invention is that of methods for manufacturing substrates that can be used to implement methods of surface-enhanced Raman spectography (SERS). The invention also relates to a substrate for surface-enhanced Raman spectography.

BACKGROUND

Surface-enhanced Raman spectography (SERS) is one of the most promising detection techniques for identifying and characterising molecules. This technique consists in depositing the molecules of interest on a substrate that has a rough metal surface. The metal surface whereon the molecules of interest are fixed is then illuminated by a monochromatic light. The molecules then emit a Raman signal characteristic of these molecules, which makes them able to be detected and identified.

However the Raman signal emitted by the molecules has an intensity that is much less than the intensity of the monochromatic light with which the molecules were illuminated.

In order to overcome this problem, it has been observed that the roughness of the metal surface of the substrate that carries the molecules of interest makes it possible to enhance the Raman signal emitted by the molecules of interest thanks to the excitation of localised plasmons of the metal (enhancement via electromagnetic effect) and by transfer of charges between the metal and the molecule adsorbed (chemical effect). This enhancement makes it possible as such to specifically detect adsorbed samples with extremely low concentrations and/or over very short periods of time.

This enhancement can be accomplished thanks to "hot spots". These hot spots are zones of the substrate where the electromagnetic field is localised and intense. For this, hot spots generally have dimensions that are less than the wavelength of the monochromatic light.

Prior art as such knows methods that make it possible to carry out hot spots on the surface of a substrate. These hot spots can be formed by cavities or by point effects. As such, the document Appl. Phys. Lett. 97, 063106 2010, Nanoletters, 9, 4505, 2009 describes hot spots formed by points. The document Nano Lett. 11, 2538, 2011; J. Vac. Sci. Technol. B 27, 2640 (2009) describes hot spots formed by cavities. However, the methods for forming hot spots of prior art use structuring technologies that can reach very high spatial resolutions and they are therefore complex and very expensive. Furthermore, they do not generally make it possible to produce substrates that have a high density of hot spots, in such a way that the increase in the light intensity emitted by the molecules of interest is limited.

SUMMARY

An aspect of the invention aims to overcome the disadvantages of prior art by proposing a method for manufacturing a substrate for surface-enhanced Raman spectography that is not aggressive, that is easy to implement, and which allows for a constant increase in the light intensity emitted by the molecules over the whole of the substrate.

Another aspect of the invention is to propose a method for manufacturing a substrate for surface-enhanced Raman spectography that can be reproduced and that is reliable, that allows for a substantial increase in the light intensity emitted by the molecules of interest and which has a high density of hot spots.

Another aspect of the invention is to propose a method for manufacturing a substrate for surface-enhanced Raman spectography that makes it possible to simultaneously carry out a large number of identical substrates.

To do this, a first aspect of the invention relates to a method for manufacturing a substrate for surface-enhanced Raman spectography, with the method comprising the following steps:
(a) creating a non-metal supporting structure on an upper surface of a support, with the supporting structure comprising at least one microstructured pattern, with the microstructured pattern comprising a top and sidewalls, with the sidewalls extending according to a direction secant to the direction of the upper surface;
(b) depositing a multilayer on the supporting structure, with the multilayer comprising at least two metal layers of the same thickness and an intermediate layer arranged between the two metal layers, with each intermediate layer being made from a material that can be selectively etched with respect to the metal layers;
(c) etching via chemical mechanical planarisation of a portion of the multilayer deposited on the top of the microstructured pattern in such a way as to expose ends of each layer of the multilayer;
(d) selective etching of the ends of the intermediate layers in such a way as to form cavities between the ends of two successive metal layers.

As such, firstly a supporting structure is carried out of which the dimensions, typically between 50 nm and 100 μm, do not make it directly possible to obtain the enhancement function of the electromagnetic field, but which is easy to carry out by known techniques. On this supporting structure, other structures are carried out with characteristic dimensions that are much smaller which this time make it possible to enhance the electromagnetic field. These second structures are carried out by successive deposits of metal layers and of intermediate layers in such a way as to form a multilayer that hugs the shape of the supporting structure. The response of the SERS substrate formed as such is perfectly predictable thanks to the carrying out of nanogaps separated by metal layers of a constant thickness on a non-metal supporting structure, which therefore does not participate in the SERS effect. A clipping is then carried out locally of the portion of the multilayer deposited on the upper portion of each pattern of the supporting structure. Clipping the portion of the multilayer by chemical mechanical planarisation makes it possible to guarantee the retaining of the thickness of the layers of the multilayer by using a perfectly anisotropic etching method, that does not round off the angles. A SERS substrate is as such obtained of which the response can be perfectly controlled and predicted. Following the step of clipping, the alternating of the layers of the multilayer is then exposed to air in such a way that there is access to each one of the layers of the multilayer. The intermediate layers of the multilayer can then be etched selectively and partially in such a way as to form cavities between the ends of two successive metal layers. The method then makes it possible to obtain micrometric patterns surrounded by metal pins of nanometric dimensions that can be perfectly controlled and reproduced, separated between them by cavities also of nanometric dimensions that can be perfectly controlled and reproduced.

The method is particularly beneficial as it makes it possible to easily carry out metal pins of nanometric dimensions separated by cavities of nanometric dimensions without resorting to aggressive etching methods. Furthermore, the width of the pins and of the cavities can be controlled and reproduced very well since it is determined by the thickness of the layers deposited and since it is not altered by the etching of the portion of the multilayer deposited on the top of the microstructured pattern. This thickness is easy to control.

The method then makes it possible to easily obtain a substrate that allows for a reinforcing of the electromagnetic field of which the response can be predicted. The intensity of the electromagnetic field obtained thanks to the substrate formed as such can as such be between 10 times and several thousands of times greater than that obtained with the substrates of prior art.

The method according to an embodiment of the invention can also have one or several of the characteristics hereinafter taken individually or according to any technically permissible combination.

In an embodiment, the intermediate layer is a dielectric layer, as dielectric layers do not absorb or absorb very little of the plasmon generated on the surface of the metal. The substrate carried out as such will therefore allow for better surface enhancement. Furthermore, the dielectric layers can easily be etched selectively with respect to the metal layers, which is beneficial during the step (d) of the method.

In an embodiment, each microstructured pattern has a height between 50 nm and 100 µm, which makes it possible to easily manufacture the microstructured pattern with the known methods.

In an embodiment, each metal layer of the multilayer has a thickness between 1 angstrom and 50 nm. The thickness of the metal layers of the multilayer will condition the width of the metal pins on the surface of the substrate.

In an embodiment, each intermediate layer of the multilayer has a thickness between 1 angstrom and 20 nm. The thickness of the intermediate layers will condition the width of the cavities between the metal pins.

In an embodiment, the multilayer has a thickness less than the height of the microstructured pattern, which makes it possible to update all of the layers during the step (c) of clipping.

In an embodiment, the layers of the multilayer are deposited according to a compliant depositing technique, which makes it possible to have a multilayer of a constant thickness over the entire surface of each microstructured pattern. The step (c) of etching is then facilitated.

In an embodiment, the sidewalls of the microstructured pattern extend according to a direction that forms an angle strictly less than 90° with a direction normal to the upper surface of the support, which makes it possible to carry out compliant deposits on the pattern more easily.

According to various embodiments, the etching carried out during the step can be carried out by chemical mechanical planarisation or by dry etching.

A second aspect of the invention relates to a substrate for surface-enhanced Raman spectography comprising:
 a support comprising an upper surface;
 a non-metal supporting structure arranged on the upper surface of the support, with the supporting structure comprising at least one microstructured pattern, with the microstructured pattern comprising a top and sidewalls, with the sidewalls extending according to a direction secant to the direction of the upper surface;
 a multilayer arranged on the sidewalls of the microstructured pattern, with the multilayer comprising at least two metal layers of the same thickness and an intermediate layer arranged between the two metal layers, with the intermediate layer being made from a material that can be selectively etched with respect to the metal layers, with each metal layer comprising an end, with the intermediate layer having an end that is set back with respect to the end of the metal layers that surround it in such a way that the ends of two successive metal layers form metal pins separated by a cavity.

Such a substrate comprises multiple hot spots on the cavities located between the ends of the metal layers, which makes it possible to substantially enhance the Raman signal emitted by the molecules of interest deposited on this substrate thanks to the excitation of localised plasmons of the metal (enhancement via electromagnetic effect). Such a substrate therefore makes it possible to increase the light intensity emitted by molecules of interest which are deposited on its surface in such a way that it allows for a faster detection of these molecules of interest.

The substrate according to the second aspect of the invention can have one or several of the characteristics hereinafter taken individually or according to any technically permissible combination.

In an embodiment, the sidewall of the microstructured pattern comprises faces separated by edges, which makes it possible to create a reinforcement of the electromagnetic field via the point effect and therefore to increase the enhancement of the Raman signal emitted by the molecules.

In an embodiment, the supporting structure comprises several microstructured patterns forming a periodic array, which makes it possible to increase the density of hot spots on the surface of the substrate, and to homogenise their distribution on the substrate. The enhancement of the Raman signal generated by the substrate is as such more substantial and more homogeneous.

In an embodiment, the metal layers have thicknesses that differ from one another, which makes it possible to obtain a progressive index gradient in such a way that the substrate will then have resonances with several incident wavelengths.

In an embodiment, the multilayer comprises several intermediate layers, with the intermediate layers having thicknesses that differ from one another, which makes it possible to obtain a progressive index gradient in such a way that the substrate will then have resonances with several incident wavelengths.

In an embodiment, each microstructured pattern has a height between 50 nm and 100 µm.

In an embodiment, each metal layer of the multilayer has a thickness between 1 angstrom and 50 nm, for example between 10 nm and 50 nm.

In an embodiment, each intermediate layer of the multilayer has a thickness between 1 angstrom and 20 nm, for example between 10 nm and 20 nm.

In an embodiment, each cavity has a depth between 1 angstrom and 200 nm, and for example between 10 nm and 100 nm.

BRIEF DESCRIPTION OF THE FIGURES

Other characteristics and benefits of the invention shall appear when reading the following detailed description, in reference to the annexed figures, which show:

FIG. 5b, an enlarged view of the portion E of the substrate of FIG. 5a;

DETAILED DESCRIPTION

FIGS. 1a to 1e show the various steps of a method according to an embodiment of the invention.

Figure 1A:
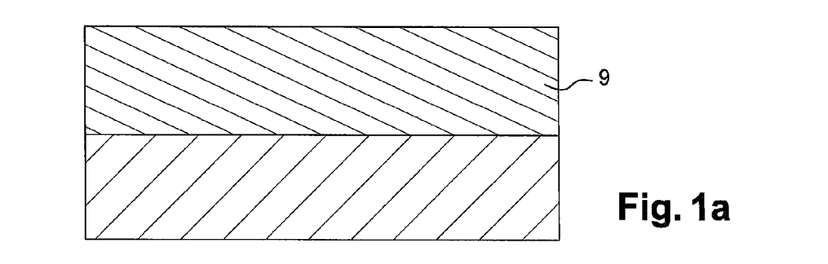
FIGS. 1a to 1e, the steps of a method according to an embodiment of the invention.

This method comprises a first step 101 of carrying out a supporting structure 2 on an upper surface 4 of a support 3. According to various embodiments, the to support 3 can be made of silicon, metal, glass.

The supporting structure 2 comprises at least one microstructured pattern 5, and in an embodiment several microstructured patterns 5. Each microstructured pattern has, in an embodiment, dimensions between 50 nm and 100 µm. Each microstructured pattern 5 has an upper portion 8, also referred to as "top" or "crest" and a sidewall 7, also referred to as "slope". The sidewall 7 of the microstructured patterns 5 extends, in an embodiment, according to a direction secant to the upper surface 4 of the support 3. The microstructured patterns 5 can have different shapes.

Figure 1B:
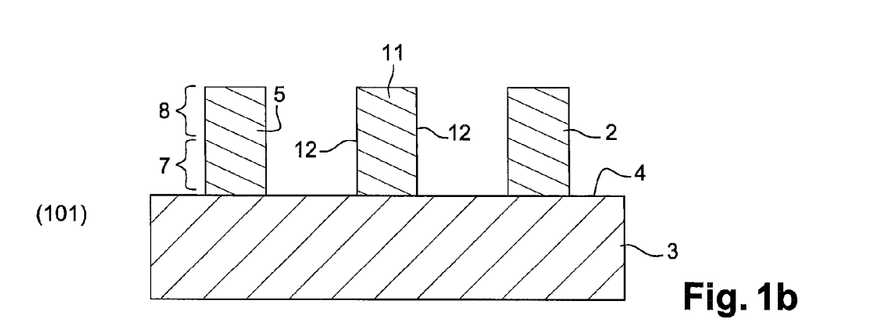

As such, according to an embodiment shown in FIG. 1b, each microstructured pattern 5 can have a parallelepiped shape. In this case, each microstructured pattern 5 comprises:

an upper wall 8 extending according to a direction substantially parallel to the upper surface 4 of the support;

a sidewall 7 extending according to a direction substantially perpendicular to the upper surface 4 of the support 3. The sidewall 7 comprises four faces 11 separated from each other by edges 12.

Figure 3A:
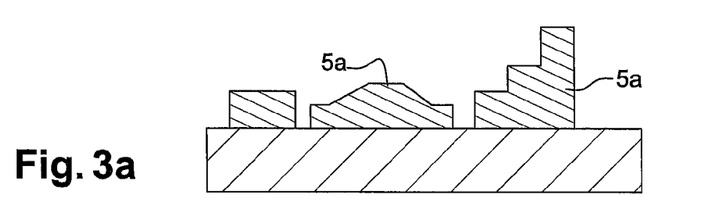
FIGS. 3a and 3b, microstructured patterns able to be used in a method according to an embodiment of the invention.
Figure 3B:
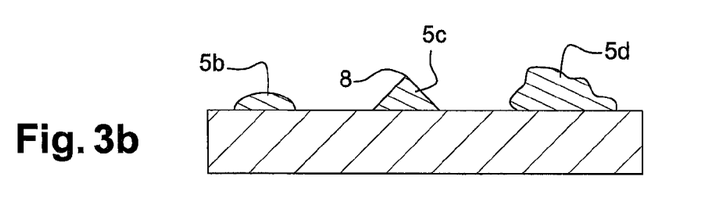

However, the microstructured patterns could also have other shapes. As such in reference to FIG. 3a, each microstructured pattern 5a could comprise several portions, having heights that are different from one another. A microstructured pattern is then obtained which has the shape of a staircase. In reference to FIG. 3b, each microstructured pattern 5b could have a dome shape, or a triangle shape, pyramid shape, or more complex shapes. According to various embodiments, the microstructured patterns of the supporting structure can all have the same shape, as shown in FIG. 1b, or they can have different shapes, as shown in FIGS. 3a and 3b.

The supporting structure 2 is, in an embodiment, comprised of polymers. Indeed, polymers have the benefit of not absorbing or absorbing very little of the plasmonic resonance of metals, in such a way that they do not reduce the enhancement of the local electromagnetic field. According to various embodiments, the supporting structure can be constituted of polymers with an acrylic base, of polymers with a poly hydroxy styrene (PHS) base or polymers with a methyl methacrylate (MMA) base. The acrylic bases make it possible to have better adherence of the metal layers on their surfaces and better mechanical resistance for the subsequent steps.

Furthermore, the polymers mentioned have the advantage to support the following steps of the method.

The supporting structure can be carried out thanks to various techniques according to the material that it is formed from. As such, when the supporting structure is made of polymer, the step of carrying out the supporting structure can comprise the following substeps:

forming of a layer of polymer 9, for example via spin-coating;

forming of microstructured patterns 5, for example via nanoimprint lithography, photolithography, electronic lithography, extreme ultraviolet lithography, interferential lithography or laser inscription.

Figure 1C:
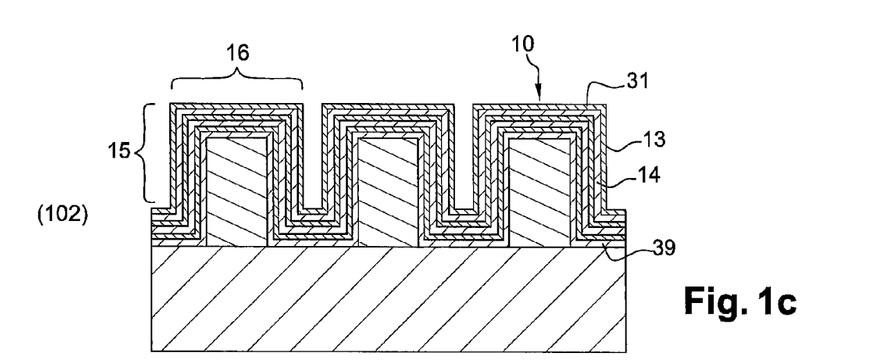

In reference to FIG. 1c, the method then comprises a step 102 of depositing a multilayer 10 on the supporting structure 2. The multilayer 10 hugs the shape of the supporting structure in such a way that it is deposited on the upper portion 8 of the microstructured patterns 5 and on their sidewall 7. The multilayer 10 therefore comprises portions 15 that extend according to a direction secant to the upper surface 4 of the support and other portions that extend according to a direction substantially parallel to the upper surface 4 of the substrate.

The multilayer 10 comprises at least two metal layers 13 of the same thickness, with two successive metal layers 13 being separated by an intermediate layer 14. Indeed, the metal layers have a response referred to as "plasmonic" when they are subjected to a determined electromagnetic radiation. The metal layers are, in an embodiment, constituted of one of the following materials: gold, silver, copper, aluminium. According to various embodiments, the metal layers can all be constituted of the same material, or they can be constituted of at least two by two with the same material. There can then be different pairs of metal layers in the multilayer which would make it possible to operate the device at different wavelengths. Moreover, the metal layers can all have the same thickness or they can have different thicknesses, which makes it possible to obtain a progressive index gradient. Indeed, by adjusting the thicknesses of each layer, the equivalent optical index of the multilayer can be varied between the optical index of the metal layers and that of the intermediate layers, as long as the sum of the thickness of a metal layer and of the thickness of an intermediate layer remains less than the incident wavelength. The substrate formed as such will then have resonances with several incident wavelengths.

The intermediate layers 14 are constituted of a material that can be selectively etched with respect to the metal layers. According to various embodiments, the intermediate layers can all be constituted of the same material, or they can be constituted of materials that differ from one another. In this latter case, all of the intermediate layers are constituted of a material that can be selectively etched with respect to the metal layers, either at the same time or one after the other with different methods. Having different cavity depths can then be considered and therefore adjust the operation and/or the resonance of the substrate obtained as such.

According to an embodiment, the intermediate layers are constituted of a dielectric material. Indeed, dielectric materials do not absorb or absorb very little of the plasmon generated on the surface of the metal layers. The choice of dielectric material can be for example silicon oxide, alumina, hafnium oxide, silicon nitride, titanium oxide, etc. Moreover, the intermediate layers can all have the same thickness or they can have different thicknesses, which makes it possible to obtain a progressive index gradient. The substrate formed as such will then have resonances with several incident wavelengths.

It can also be considered to carry out the intermediate layers in metal materials. However, in this case, the depth of the cavities grooved into the intermediate layers should be more substantial than in the preceding embodiment, in such a way that the intermediate layer does not absorb the plasmon generated on the surface of the metal layers.

The layers of the multilayer are in an embodiment deposited by a compliant depositing method in such a way that the thickness of the multilayer is substantially the same over the entire surface of the microstructured patterns. For this, the layers of the multilayer can be deposited by physical vapour deposition, using an inclined bombardment beam, by turning the sample.

During the step of depositing the multilayer, the first layer deposited on the microstructured patterns, which shall be called "inside layer" 39, can be a metal layer or this can be an intermediate layer. Likewise, the last layer deposited, which shall be called "outside layer" 31, can be a metal layer or this can be an intermediate layer. Having as an outside layer 31 an intermediate layer makes it possible to protect the active metal layer from subsequent methods and/or from the risks of a chemical reaction with the atmosphere or from mechanical damage of the scratching type during the manipulation of the substrate.

Figure 1D:
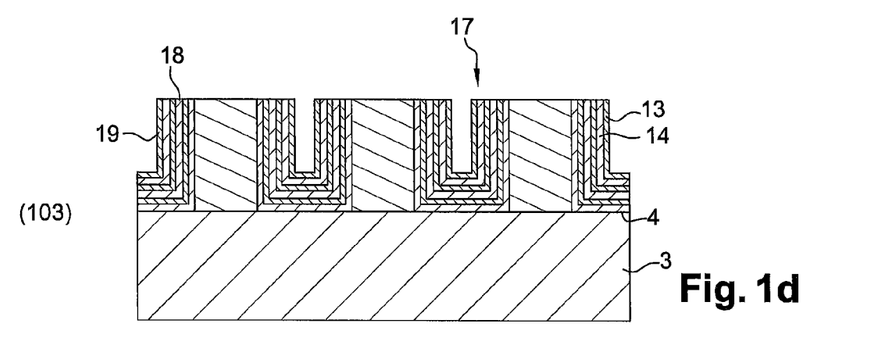

In reference to FIG. 1d, the method then comprises a step 103 of etching a portion of the multilayer deposited on the upper portion 8 of each microstructured pattern 5. This step is referred to as "step of clipping". Indeed, it comprises a step of etching of the portion of the multilayer deposited on the crest of each one of the microstructured patterns. This step can also comprise a step of etching of a portion of the crest of each microstructured pattern. In the embodiment of FIG. 1d, the portion 16 of the multilayers deposited on the upper surface 8 of the microstructured patterns is etched. For this, the regions of the multilayers which are parallel to the upper surface 4 of the support can for example be etched, while etching slower the regions of the multilayer which are inclined with respect to the upper surface 4 of the support. This step of etching 103 is carried out by chemical mechanical planarisation (CMP). This etching technique makes it possible to obtain edges that are not rounded and to not modify the thickness of the layers.

At the end of this step columns are obtained 17 extending according to a direction secant to the upper surface 4 of the support 3, with each column 17 comprising an alternating of metal layers and of intermediate layers. The upper ends 18 of each metal layer and the upper ends 19 of each intermediate layer are exposed to the air and they can therefore be accessed for the rest of the steps of the method.

Figure 4D:
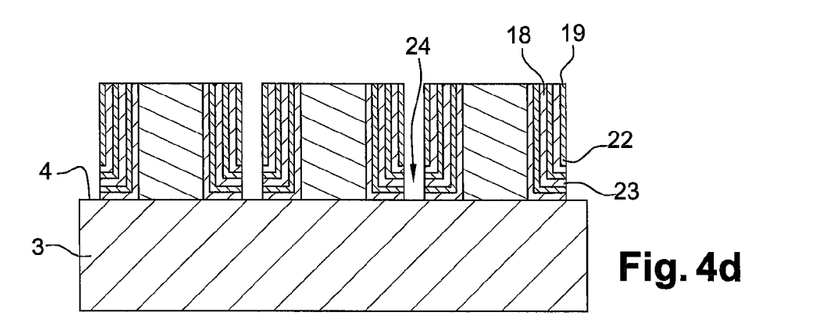
FIGS. 4d and 4e, steps alternative to the steps shown in FIGS. 1d and 1e.

Alternatively, in reference to FIG. 4d this step 103 of etching portions of the multilayer arranged on the upper portion 8 of the microstructured patterns can also comprise a step of etching horizontal portions 24 of the multilayer arranged on the surface 4 of the support. As such not only an access to the upper ends 18 and 19 of the intermediate layers and of the metal layers is obtained, but also to their lower ends 22 and 23, which will be useful to carry out a step of double etching, as shall be seen in what follows in reference to FIG. 4e.

Figure 1E:
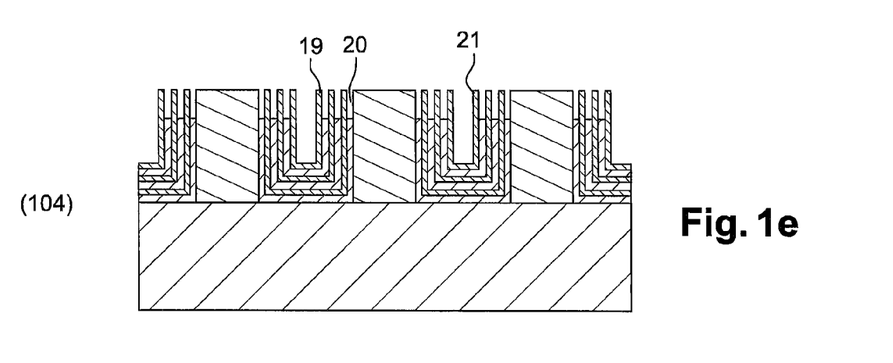

In reference to FIG. 1e, the method then comprises a step 104 of selective etching of a portion of the intermediate layers 14 in such a way as to form cavities of air 20 between the ends 19 of two successive metal layers 13. More precisely, during this step, the ends 18 of the intermediate layers 14 are selectively etched in relation to the ends 19 of the metal layers 13 in such a way that, at the end of this step, the ends 19 of the metal layers are separated by cavities of air 20. This step of etching is partial in such a way as to retain a portion of the intermediate layers between the metal layers which makes it possible to maintain the metal layers in place without them collapsing on one another and also to have cavities of air with a controlled depth. The technique used to selectively etch the intermediate layers depends on the material chosen for the intermediate layers and for the metal layers. According to various embodiments, the technique chosen can be a dry or wet etching technique.

Figure 4E:
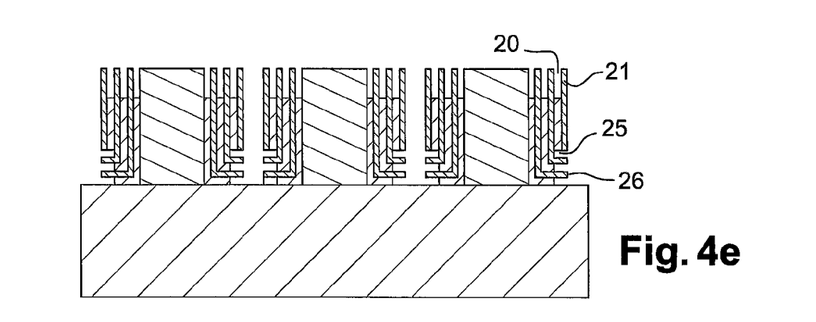

Alternatively, in reference to FIG. 4e, the step 104 of selective etching can be a step of double etching during which the upper ends 18 of the intermediate layers are selectively etched, but also the lower ends 22 of the intermediate layers. Two times more metal pins and two times more cavities are thus obtained: indeed, as hereinabove vertical metal pins 21 are obtained separated by vertical cavities of air 20 and horizontal metal pins 26 separated by horizontal cavities of air 25. As hereinabove, this step of double etching can be carried out by dry or wet etching.

The method makes it possible to manufacture a substrate that can be used in the framework of surface-enhanced Raman detection. Indeed, on the surface of the substrate microstructured patterns 5 are as such obtained surrounded by metal pins 21, 26 of nanometric dimensions, separated by cavities of air also of nanometric dimensions. Each cavity of air obtained at the end of the method has in an embodiment a width between 1 angstrom and 20 nm and a depth between 10 nm and 100 nm. Each metal pin obtained at the end of the method has in an embodiment a width between 10 nm and 50 nm.

The method can then comprise a step of depositing molecules of interest on the surface of the substrate obtained as such. The molecules of interest are then deposited on the surface of the metal pins and in the cavities of air. The materials chosen to carry out the supporting structure can be chosen according to their surface energy, in such a way as to control the depositing of the molecules which will then be deposited on the substrate. The depositing of molecules at certain locations of the substrate rather than at other locations can as such be favoured.

Figure 2C:
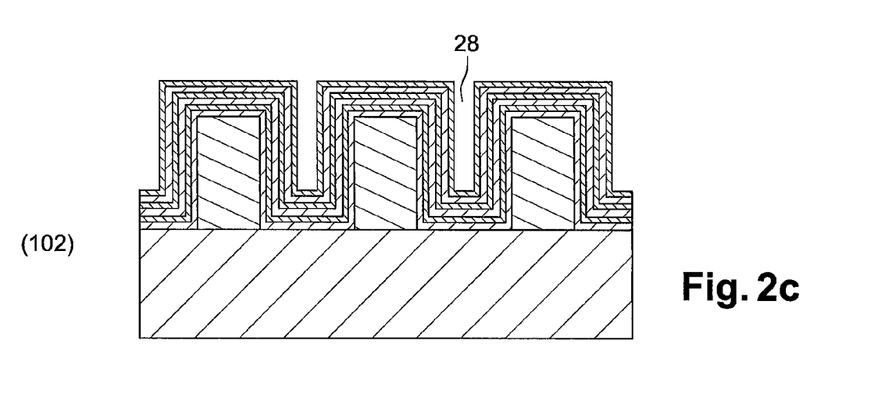
FIGS. 2c to 2e, steps of a method according to another embodiment of the invention.
Figure 2D:
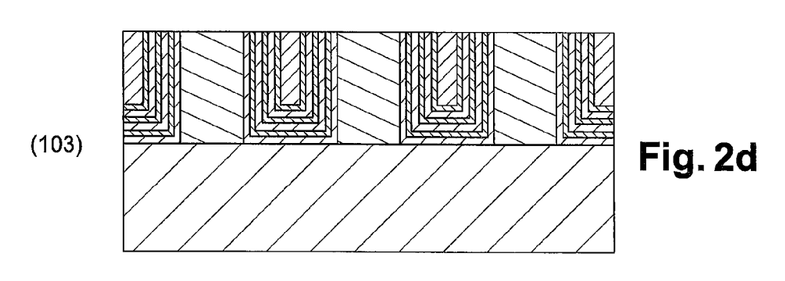
Figure 2E:
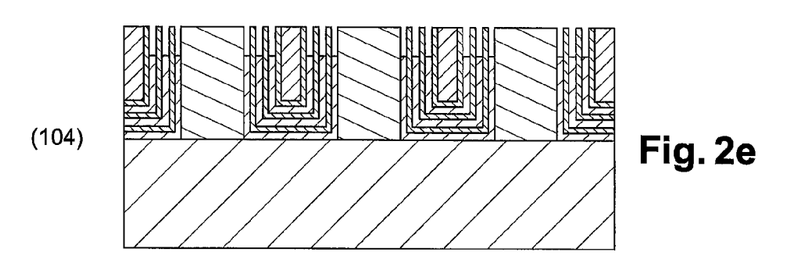

The invention is not limited to the embodiment described hereinabove. As such, as shown in FIGS. 2c to 2e, the method described in reference to FIGS. 1a to 1e could also comprise, following the step 102 of depositing of the multilayer 10, an additional step 102b is of depositing a dielectric material 27 in the spaces 28 formed between the microstructured patterns 5 covered by the multilayer 10. This dielectric material 27 makes it possible to fill in the empty space between the microstructured patterns which makes the step of clipping by chemical mechanical planarisation easier and more controllable. Moreover as this space is filled in the residues formed during the step of clipping will not be lodged in the empty spaces and can subsequently be easily removed by surface cleaning methods. In the opposite case removing these residues can be impossible or very complicated and the latter could disturb the proper operation of the substrate. The dielectric material 27 deposited in the spaces 28 can be for example silicon oxide or silicon nitride. The later steps 103, 104 of the method are identical to those described hereinabove.

The method according to an embodiment of the invention is particularly beneficial since it makes it possible to obtain metal pins separated by cavities with dimensions that can be precisely controlled. Indeed, the width w1 of the metal pins 21 obtained is controlled by controlling the thickness of the metal layers 13 deposited. Likewise, the width w0 of the cavities 20 of air is controlled by controlling the thickness of the intermediate layers 14 deposited. The width of the pins and of the cavities can therefore be controlled easily and precisely since the thickness of the layers deposited is also as such. Moreover, the depth P0 of the cavities of air can be controlled by controlling the etching of the end of the intermediate layers 20 which it too is also easy to control. Furthermore, when the intermediate layer is made of dielectric material, the method does not use a step of aggressive etching since the intermediate layer can easily be etched by dry or chemical etching.

Figure 5A:
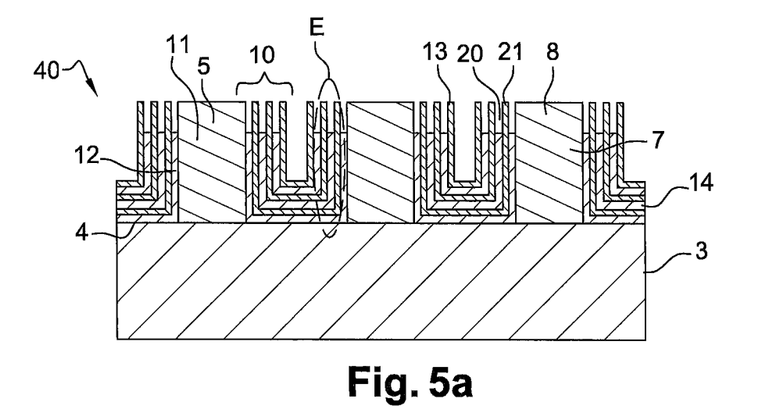
FIG. 5a, a diagrammatical representation of a substrate according to an embodiment of the invention.
Figure 5B:
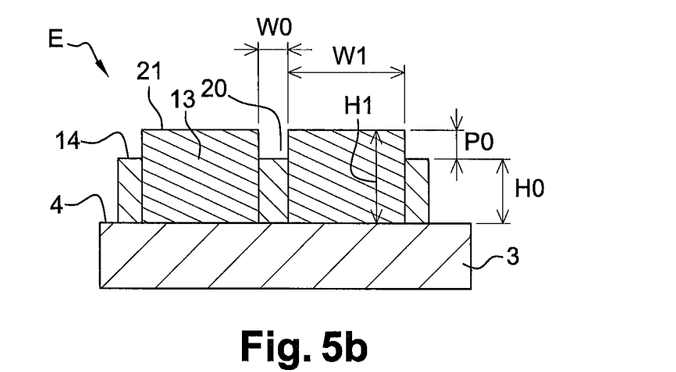

Dimensioning of the Metal Pins and of the Cavities:

A method for dimensioning the metal pins 21 and the cavities 20 that separate them shall now be described in reference to FIGS. 5a and 5b.

The dimensions for the pins and the cavities are chosen in order to obtain a resonance of the electromagnetic field.

These dimensions can be determined according to the method explained hereinafter.

First the incident wavelength of the monochromatic light that will be sent over the molecules to be detected is chosen. This incident wavelength can be chosen according to the molecules to be detected and/or according to the equipment available to the user. In this embodiment, an incident wavelength of 785 nm for example is chosen.

The materials that will constitute the metal layers and the intermediate layers of the multilayer 10 are then chosen. These materials can be chosen according to the methods of depositing available, and/or for reasons of chemical affinities with the molecules to be detected, and/or according to the absorption properties of these materials with regards to the incident wavelength. In this embodiment, it is chosen for example to carry out metal layers made of gold and the intermediate layers made of $SiO_2$.

The method then comprises a step of dimensioning cavities 20 and metal pins 21 according to the incident wavelength chosen and materials chosen for the multilayer. Indeed, it is possible to determine the dimensions of the pins and of the cavities in such a way that the substrate has a resonance at the incident wavelength. For this, the dimensions of the cavities 20 and of the pins 21 that minimise the reflectivity of the substrate and therefore which maximise the reinforcing of the electromagnetic field are determined. A method called RCWA (rigorous coupled wave analysis) or a method called FDTD for "finite difference time domain" can for example be used for this. These methods make it possible to simulate the reflectivity of a surface according to its geometry and its composition.

Figure 6:
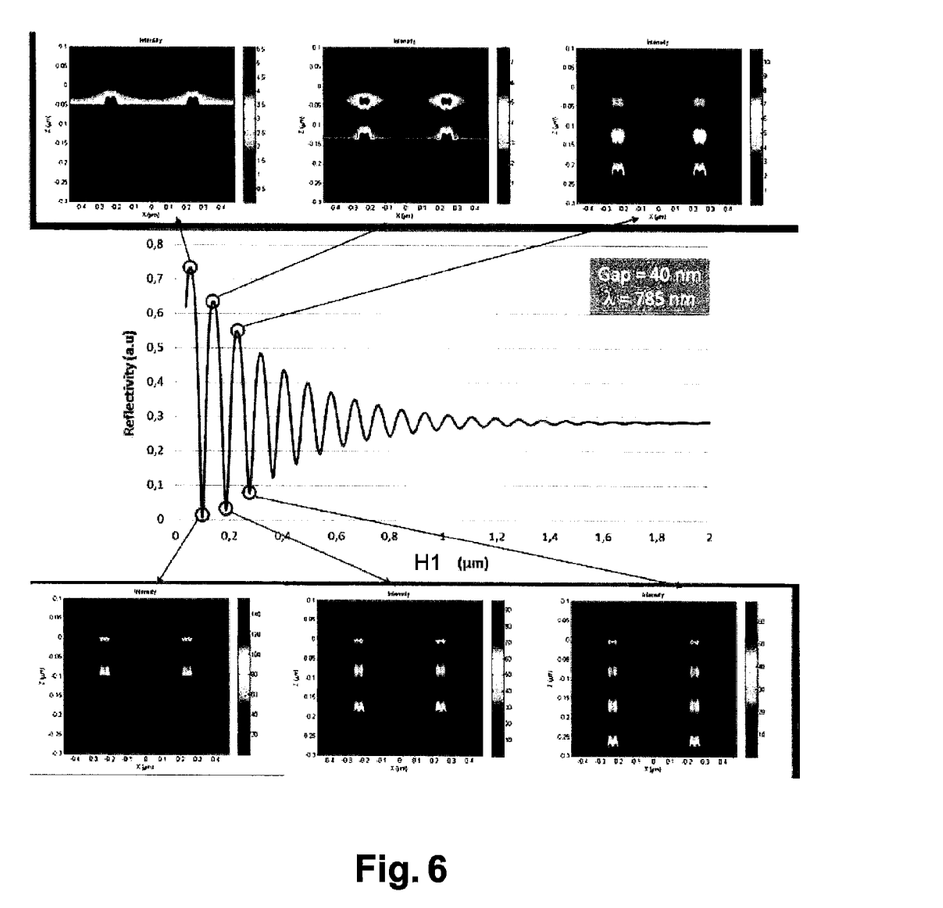
FIG. 6, a curve showing the reflectivity of a substrate according to an embodiment of the invention for an incident wavelength of 785 nm, according to the height H1 of the metal pins of this substrate, when these metal pins have a length W1=40 nm, and when the air gaps between these pins have a depth P0=40 nm and a width W0=7.3 nm.

As such, FIG. 6 shows as such the change, according to the height H1 of the metal pins, of the reflectivity of a structure comprising an alternating of layers made of gold and of silica for an incident wavelength of 785 nm, when the metal pins have a width W1=40 nm, the cavities have a width W0 of 7.3 nm and a depth P0 of 40 nm. It can then be seen that the structure obtained can have a minimum of reflectivity for a height H1 equal to 99 nm or 187 nm, or 275 nm, etc. One of these heights for the metal pins H1 can therefore be chosen.

Figure 7:
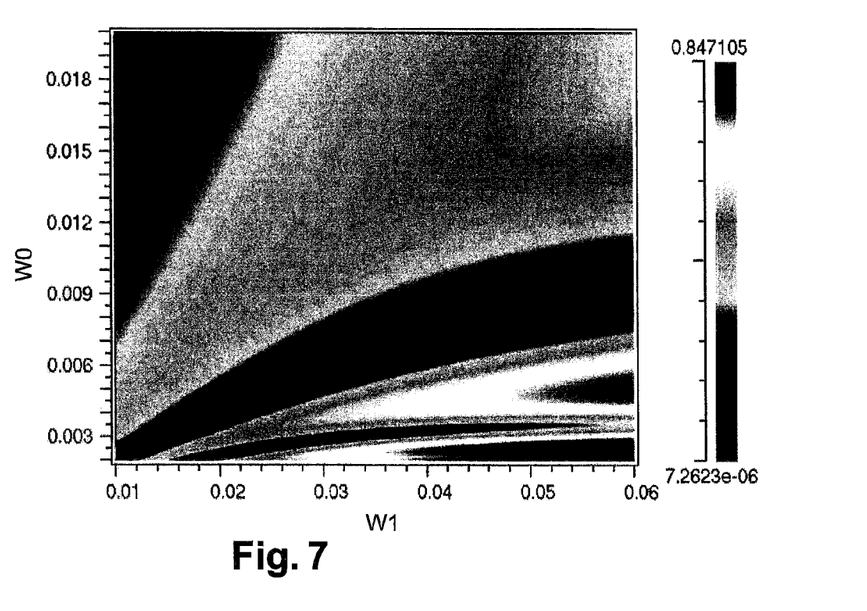
FIG. 7, a diagram showing the change in the reflectivity of a substrate according to an embodiment of the invention for an incident wavelength of 785 nm, according to the width W1 of the metal pins of this substrate and of the width W0 of the cavities between these metal pins, when these metal pins have a height H1=100 nm and when the cavities have a depth P0=40 nm.

FIG. 7 shows another simulation carried out by a RCWA (for "rigorous coupled wave analysis) method wherein:
the incident wavelength is set to 785 nm,
the metal layers are comprised of gold,
the intermediate layers are comprised of silica,
the height H1 of the pins is set to 100 nm;
the depth P0 of the cavities is set to 40 nm.
This time the change in the reflectivity of the substrate is examined according to the width W1 of the pins and of the width W0 of the cavities. It is observed that the minimum in reflectivity is reached when W1 and W0 comply with the following logarithmic law:

$$W0 = 439 \ln(W1) - 1909,$$

with W1 and W0 in microns.

Figure 8:
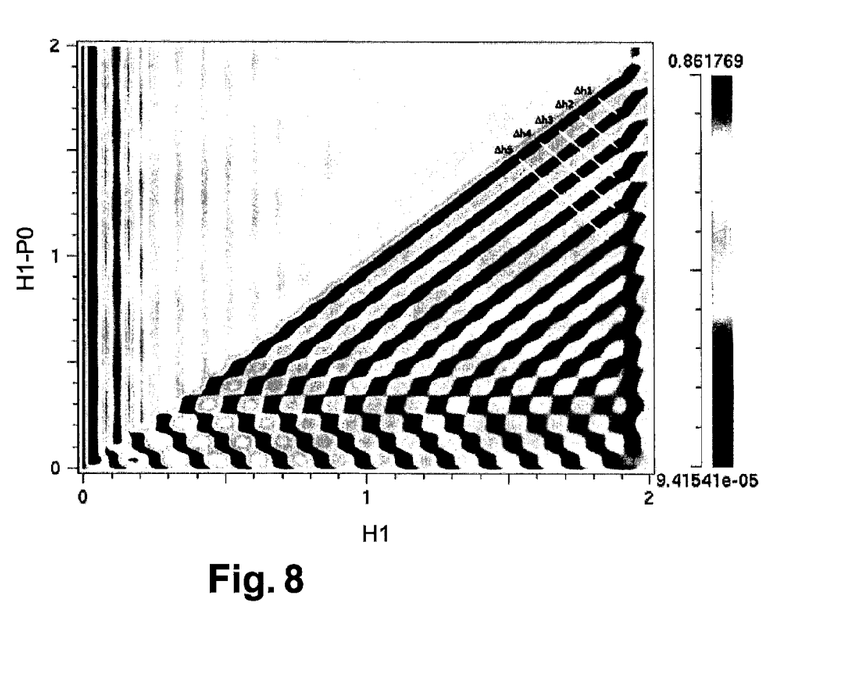
FIG. 8, a diagram showing the change in the reflectivity of a substrate according to an embodiment of the invention for an incident wavelength of 785 nm, according to the height H1 of the metal pins of this substrate and of the height H1-P0 of the cavities between these metal pins, when these metal pins have a length W1=40 nm and when the cavities have a width W2=7.3 nm.

FIG. 8 shows another simulation carried out wherein this time the widths W1 of the pins and those W0 of the cavities have been set and the optimum heights are sought in such a way as to have the minimum of reflectivity. As such, this simulation was carried out by a RCWA (for "rigorous coupled wave analysis) method wherein:
the incident wavelength is set to 785 nm,
the metal layers are comprised of gold,
the intermediate layers are comprised of silica,
the width of the pins is set to 40 nm;
the width of the cavities is set to 7.3 nm.

These simulations therefore make it possible to determine:

the width W1 of the pins and therefore the thickness of the metal layers deposited;
the width W0 of the cavities and therefore the thickness of the intermediate layers deposited;
the height H1 of the pins and therefore the height of the microstructured patterns at the end of the step 103;
the depth P0 of the cavities and therefore the duration of the etching of the end of the intermediate layers.

Simulations can also be carried out in order to determine the number of layers in the multilayer. These simulations are identical to those shown hereinabove except that instead of considering only two metal layers and one intermediate layer, a larger number of layers is taken into consideration in such a way as to identify or not modes of coupling between the various repetitions of layers, which may or may not modify the optimal geometries somewhat. The optimum thickness of the multilayer 10 is as such deduced from this.

Choice of the Supporting Structure:

The method then comprises a step of determining the supporting structure.

Figure 9A:
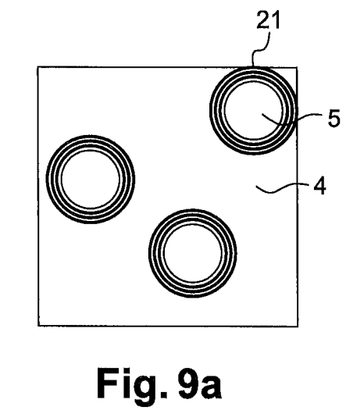
FIGS. 9a and 9b, top views of substrates according to a first and a second embodiment of the invention.
Figure 9B:
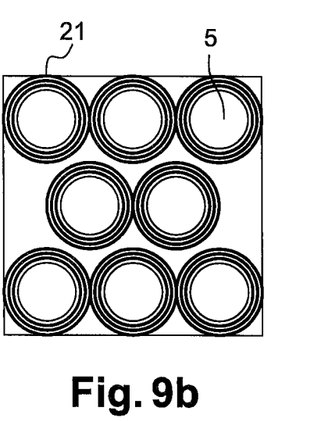

The supporting structure comprises in an embodiment several microstructured patterns 5 on which the multilayer will be deposited. These microstructured patterns 5 can be isolated from one another as shown in FIG. 9a or they can form an array as shown in FIG. 9b. Having microstructured patterns that form an array makes it possible to have a greater density of hot spots.

Figure 10A:
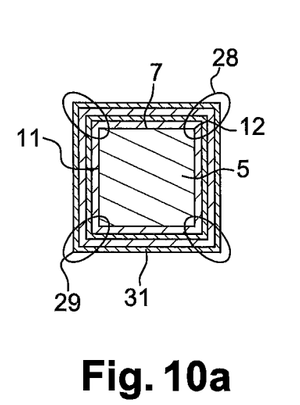
FIGS. 10a and 10b, top views of substrates according to two other embodiments of the invention.
Figure 10B:
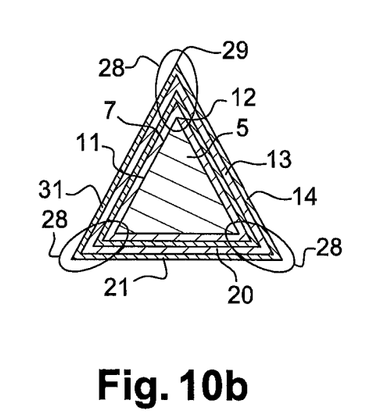

The shape of each microstructured pattern 5 can also be determined by simulating the response that the substrate will have according to the shape chosen. These simulations can also be carried out with a rigorous coupled wave analysis method or a finite difference time domain method. As such, in reference to FIGS. 10a and 10b, the shape of the sidewalls 7 of the microstructured patterns 5 is in an embodiment chosen in such a way that the sidewalls 7 comprise faces 11 separated from each other by edges 12. The angle of these edges 12 is determined in such a way that the supporting structure, once covered by the multilayer 10, generates a reinforcing of the electromagnetic field via the point effect in zones 28 located in the vicinity of the edges 12. More precisely, the outer metal layer 31 of the multilayer that covers the microstructured patterns also forms edges 29 where the sidewall 7 of the microstructured patterns forms edges 12. The edges 29 of the outer metal layer 31 therefore generate point effects and therefore reinforcing zones 28 of the electromagnetic field.

Figure 11:
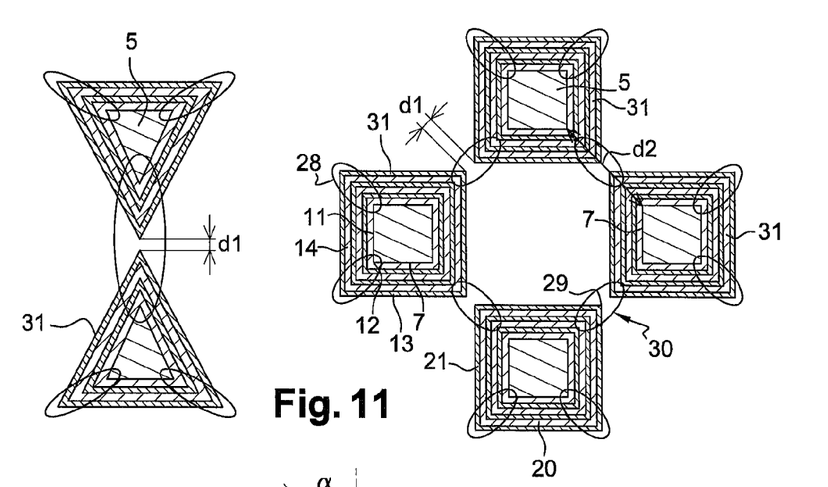
FIG. 11, a top view of a substrate according to another embodiment of the invention.

Moreover, in reference to FIG. 11, the separation between two adjacent microstructured patterns can also be determined, by simulations with electromagnetic calculation software, in such a way as to optimise the coupling effects between adjacent microstructured patterns in such a way as to increase the reinforcing of the electromagnetic field. More precisely, by optimising the distance between the edges 29 of the outer metal layer 31 that surround two adjacent microstructured patterns, the reinforcing of the electromagnetic field can be optimised further by coupling the point effect generated by the edges 29 and the confinement of the electromagnetic field created in the space 30 formed between these two edges 29. This optimisation of the distance d1 between the edges 29 of the outer metal layer 31 is in an embodiment carried out thanks to an electromagnetic calculation software. This distance d1 is in an embodiment between 1 nm and 50 nm. Once the distance d1 is set, as the thickness of the multilayer 10 was set hereinabove during the step of dimensioning the cavities and the pins, the distance d2 between the edges 12 of two adjacent microstructured patterns 5 is deduced from this.

Figure 12:
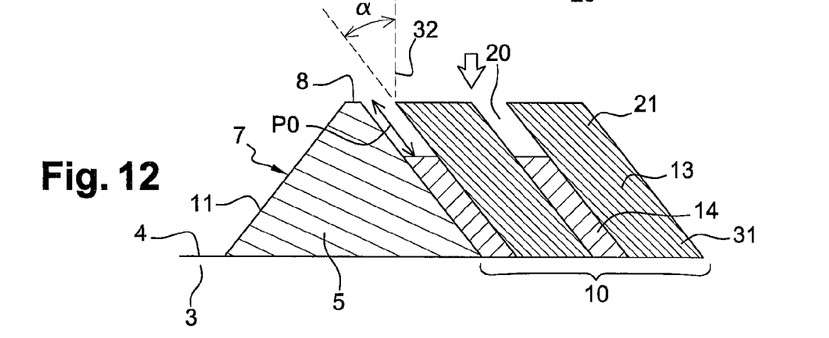
FIG. 12, a cross-section view of a microstructured pattern of a substrate according to an embodiment of the invention.
Figure 13:
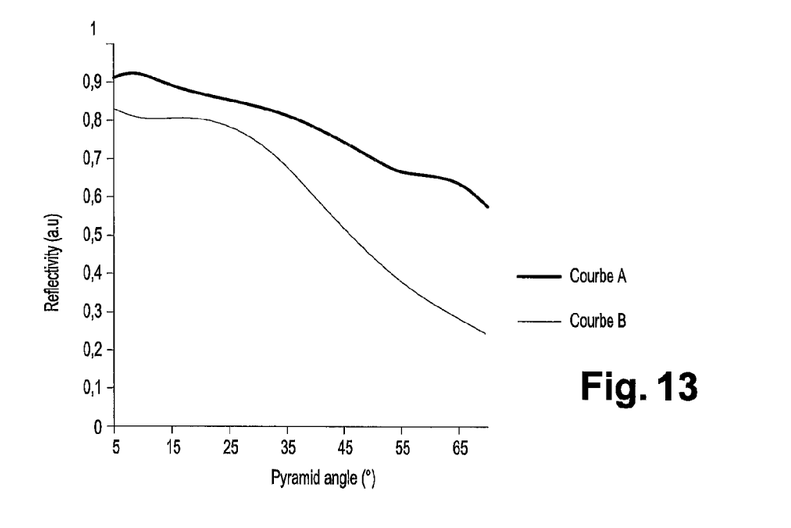
FIG. 13, the resulting reflectivity curve of an incident wave at 785 nm on the substrate of FIG. 12, according to the angle α of inclination of the sidewalls of the microstructured patterns of this substrate in the cases where the microstructured pattern is covered only by a metal layer of gold (curve A) and in the case where the microstructured pattern is covered by a multilayer comprising two metal layers of gold of 40 nm of thickness and two intermediate layers made of silicon oxide of 20 nm in thickness, with the cavities between the metal pins having a depth P0 of 100 nm.

In reference to FIG. 12, the angle α formed between the sidewalls 7 of each microstructured pattern 5 and an axis of reference 32 perpendicular to the upper surface 4 of the support can also be optimised so as to minimise the reflectivity of the substrate formed as such. As such, FIG. 13 shows the change in the resulting reflectivity of an incident wave at 785 nm according to the angle α:

of a microstructured pattern 5 in the shape of a pyramid covered by a layer of gold of 160 nm (curve A);
of a microstructured pattern 5 in the shape of a pyramid covered by a multilayer 10 comprising
two stacks with each one comprising:
a metal layer 13 made of gold of 40 nm;
an intermediate layer 14 made of silicon oxide of 20 nm in thickness;
a metal layer made of gold of 40 nm in thickness.
The cavities 20 formed between two successive metal pins 21 each having a depth P0 of 100 nm (curve B).

It is observed in this figure that the more the angle α increases, the more the reflectivity of the substrate decreases. Indeed, the microstructured patterns that have inclined sidewalls with respect to the normal to the plane of the support have the benefit, after selective etching of the end of the intermediate layers in relation to the ends of the metal layers, the cavities formed have openings that are not parallel to the surface 4 of the support 3 which allows for an optimum use of the substrate if the incident monochromatic wave is not emitted according to a direction normal to the upper surface of the support. Indeed, the coupling between the incident wave and each cavity depends substantially on the angle between the opening of the cavity and the direction of the monochromatic wave. The reflectivity decreases when the angle of the pyramid is accentuated. This phenomenon is all the more so marked for structures with cavities.

Figure 14A:
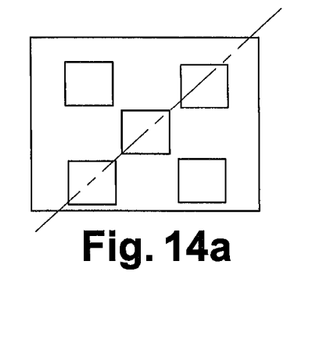
FIGS. 14a to 14f, views of a substrate according to an embodiment of the invention during a method of carrying out this substrate.
Figure 14B:
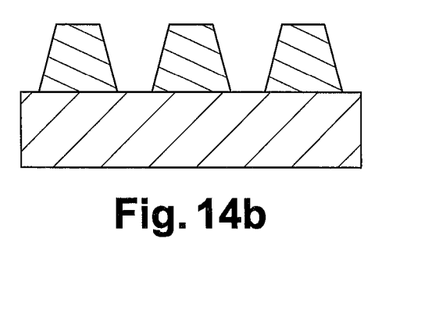
Figure 14C:
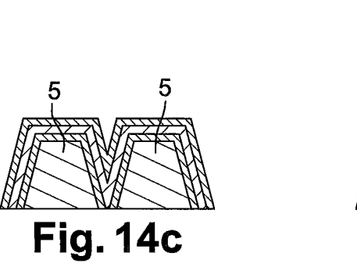
Figure 14D:
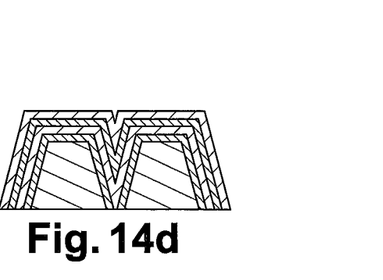
Figure 14E:
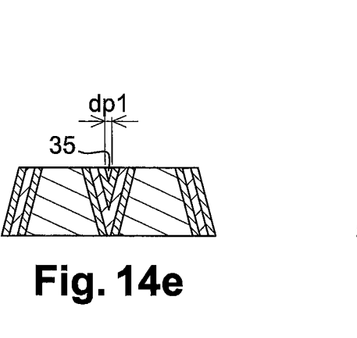
Figure 14F:
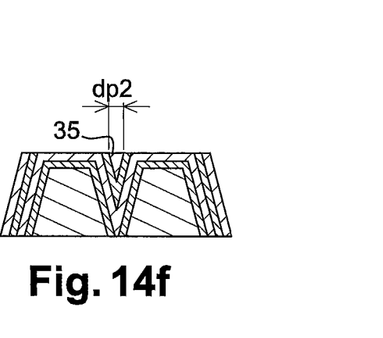
Figure 15A:
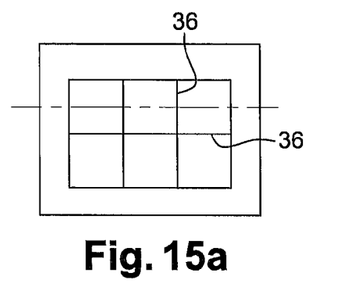
FIGS. 15a to 15d, views of a substrate according to another embodiment during a method of carrying out this substrate.
Figure 15B:
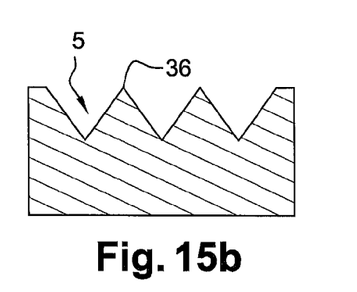
Figure 15C:
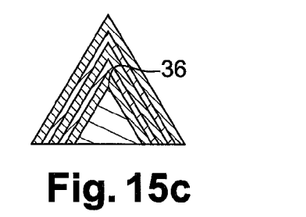
Figure 15D:
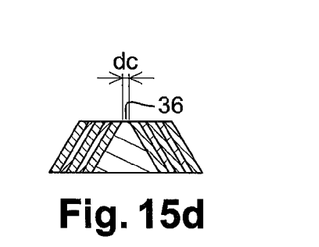

It can also be chosen to carry out a supporting structure that protrudes from the surface of the support as shown in FIGS. 14a to 14f, or it can be chosen to carry out a supporting structure grooved into the support or into a layer deposited on the support, as shown in FIGS. 15a to 15d. In the case of a protruding supporting structure, hot spots are created by the gaps 35 formed between the multilayers deposited on two adjacent microstructured patterns 5 as shown in FIGS. 14e and 14f. The distance dp1 between these multilayers can be calculated so as to optimise the amplification of the electromagnetic field in this zone. In the case of a supporting structure that is grooved, hot spots are created by the point effect on the upper end 36 of the edges that separate two adjacent microstructured patterns 5. The width dc of this edge 36 is also calculated so as to optimise the amplification of the electromagnetic field obtained.

Dimensioning of the Supporting Structure:

The dimensions of the supporting structure as well as the materials that constitute it can be chosen in such a way that the supporting structure forms a photonic crystal. This photonic crystal will make it possible to reinforce the optical coupling between the surface of the sample (with the nanogaps) and the incident laser.

In practice the photonic crystal can be dimensioned with a calculation software and it allows the incident laser arriving on the surface in practically normal incidence to be redirected in the plane of the substrate which makes it possible to substantially increase the length of interaction between the incident laser and the nanogaps.

Dimensioning of the Microstructured Patterns:

Once the shape of the supporting structure is determined, the method comprises a step of determining the dimensions of the microstructured patterns of the supporting structure. The choice of these dimensions does not necessarily require a calculation of the reinforcing of the electromagnetic waves, outside of the height of these patterns which is determined in such a way as to have the height H1 desired for the metal pins. The other dimensions of the microstructured patterns are in an embodiment determined according to:

- the technological capacity of the methods used to carry out these patterns during the step 101;
- the technological capacity of the etching methods used during the step 103;
- the technological capacity of the depositing methods for their ability to planarise an existing structure if the thickness deposited is excessive. Indeed, if the microstructured patterns are too high; it is more complicated to have a compliant deposit over the entire height of each pattern as each step of depositing, in particular if it is carried out by PVD or evaporation, is not perfectly compliant and there is a slight deformation in the shape of the resulting structure after each deposit and therefore as the deposit takes place there can be a planarisation of the structure which is not sought.

Figure 16A:
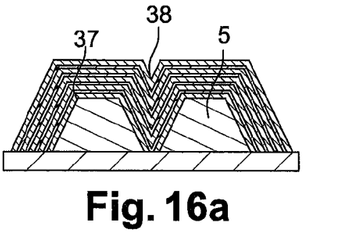
FIGS. 16a and 16b, views of a substrate during the steps (102) and (103) of a method according to an embodiment of the invention.
Figure 16B:
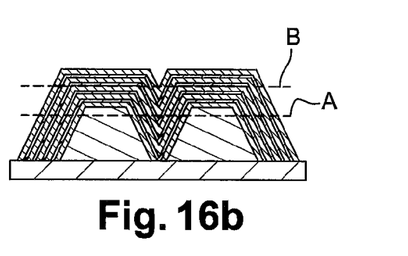
Figure 16C:
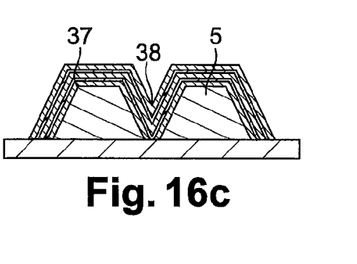
FIGS. 16c and 16d, views of another substrate during the steps (102) and (103) of a method according to an embodiment of the invention.
Figure 16D:
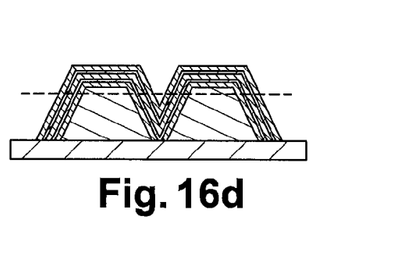

Moreover, in reference to FIGS. 16c and 16d, the height of the microstructured patterns 5 is in an embodiment chosen in such a way that after depositing of the multilayer the highest point 37 of the first layer deposited will be higher than the lowest point 38 of the last layer deposited. As such, after the step of clipping, all of the layers of the multilayer will be updated. In the opposite case, shown in FIGS. 16a and 16b, a portion of the layers of the multilayer will not be able to be used for the manufacture of the cavities, since:

- either they will be entirely suppressed during the step of clipping. This is the case if the clipping is done according to the line A;
- or they will not be used at all because they are entirely covered by other layers. This is the case if the clipping is done according to the line B.

Naturally, the invention is not limited to the embodiments described in reference to the figures and alternatives can be considered without leaving the scope of the invention.

The invention claimed is:

1. A method for manufacturing a substrate for surface-enhanced Raman spectography, the method comprising:
    creating a non-metal supporting structure on an upper surface of a support, with the supporting structure comprising at least one microstructured pattern, the microstructured pattern comprising a top and sidewalls, with the sidewalls extending according to a direction secant to a direction of the upper surface;
    depositing a multilayer on the supporting structure, with the multilayer comprising at least two metal layers of the same thickness and an intermediate layer arranged between the two metal layers, with each intermediate layer being carried out in a material that can be selectively etched with respect to the at least two metal layers;
    etching via chemical mechanical planarisation a portion of the multilayer deposited on the top of the microstructured pattern in such a way as to expose ends of each layer of the multilayer;
    selective etching the ends of the intermediate layers in such a way as to form cavities between the ends of two successive metal layers.

2. The method according to claim 1, wherein the intermediate layer is a dielectric layer.

3. The method according to claim 1, wherein each microstructured pattern has a height between 50 nm and 100 µm.

4. The method according to claim 1, wherein the multilayer has a thickness less than the height of the microstructured pattern.

5. The method according to claim 1, wherein the metal and intermediate layers of the multilayer are deposited according to a compliant depositing technique.

6. The method according to claim 1, wherein the sidewalls of the microstructured pattern extend according to a direction that forms an angle that is strictly less than 90° with a direction normal to the upper surface of the support.

7. A substrate for surface-enhanced Raman spectography comprising:
    a support comprising an upper surface;
    a non-metal supporting structure arranged on the upper surface of the support, with the supporting structure comprising at least one microstructured pattern, the microstructured pattern comprising a top and sidewalls, with the sidewalls extending according to a direction secant to a direction of the upper surface;
    a multilayer arranged on the sidewalls of the microstructured pattern, with the multilayer comprising at least two metal layers of the same thickness and an intermediate layer arranged between the two metal layers, with the intermediate layer being made from a material that can be selectively etched with respect to the metal layers, with the intermediate layer having an end that is set back with respect to the end of the metal layers that surround it in such a way that the ends of two successive metal layers form metal pins separated by a cavity.

8. The substrate according to claim 7, wherein the intermediate layer is a dielectric layer.

9. The substrate according to claim 7, wherein the sidewall of the microstructured pattern comprises faces separated by edges.

10. The substrate according to claim 7, wherein the supporting structure comprises several microstructured patterns forming a periodic array.

11. The substrate according to claim 7, wherein the multilayer comprises several intermediate layers, with the intermediate layers having thicknesses that differ from one another.

12. The substrate according to claim 7, wherein each microstructured pattern has a height between 50 nm and 100 µm.

13. The substrate according to claim 7, wherein each metal layer has a thickness between 1 angstrom and 50 nm.

14. The substrate according to claim 13, wherein each metal layer has a thickness between 10 nm and 50 nm.

15. The substrate according to claim 7, wherein each intermediate layer of the multilayer has a thickness between 1 angstrom and 20 nm.

16. The substrate according to claim 15, wherein each intermediate layer of the multilayer has a thickness between 10 nm and 20 nm.

17. The substrate according to claim 7, wherein each cavity has a depth between 1 angstrom and 200 nm.

18. The substrate according to claim 17, wherein each cavity has a depth between 10 nm and 200 nm.

* * * * *